United States Patent [19]

Tegeler et al.

[11] Patent Number: 5,145,844
[45] Date of Patent: Sep. 8, 1992

[54] METHODS OF USING HYDROXY-, ALKOXY- AND BENZYLOXY-SUBSTITUTED PHOSPHOLIPIDS TO TREAT PHOSPHOLIPASE A$_2$-MEDIATED CONDITIONS AND TO ALLEVIATE PAIN

[75] Inventors: John J. Tegeler, Bridgewater, N.J.; Kirk D. Shoger, Minneapolis, Minn.

[73] Assignee: Hoechst-Roussel Pharmaceuticals Incorporated, Somerville, N.J.

[21] Appl. No.: 664,695

[22] Filed: Mar. 5, 1991

Related U.S. Application Data

[60] Division of Ser. No. 367,926, Jun. 15, 1989, Pat. No. 5,030,783, which is a continuation-in-part of Ser. No. 76,966, Jul. 23, 1987, abandoned.

[51] Int. Cl.$^5$ ............................................. A61K 31/685
[52] U.S. Cl. ..................................................... 514/77
[58] Field of Search ........................................... 514/77

[56] References Cited

U.S. PATENT DOCUMENTS

| | | |
|---|---|---|
| 4,119,714 | 10/1978 | Kay et al. |
| 4,159,988 | 7/1979 | Eibl et al. |
| 4,372,949 | 2/1983 | Kodama et al. |
| 4,492,659 | 1/1985 | Boises et al. |
| 4,699,990 | 10/1987 | Wissner et al. ............ 558/169 |
| 4,894,367 | 1/1990 | Wissner et al. ............ 514/78 |

FOREIGN PATENT DOCUMENTS

| | | |
|---|---|---|
| 7695320 | 7/1970 | Belgium. |
| 7695330 | 7/1970 | Belgium. |
| 0040039 | 11/1981 | European Pat. Off. |
| 050460 | 4/1982 | European Pat. Off. |
| 0138558 | 4/1985 | European Pat. Off. |
| 2033358 | 7/1970 | Fed. Rep. of Germany. |
| 2033357 | 1/1972 | Fed. Rep. of Germany. |
| 2619715 | 11/1977 | Fed. Rep. of Germany. |

OTHER PUBLICATIONS

Tetrahedron Letters, vol. 22, No. 31, pp. 2949–2952, 1981.

*Primary Examiner*—Marianne M. Cintins
*Assistant Examiner*—Rebecca Cook
*Attorney, Agent, or Firm*—Elliott Korsen

[57] ABSTRACT

Novel hydroxy-,alkoxy-and benzyloxy-substituted phospholipids, a process for the preparation thereof, and methods for treating pain, phospholipase A$_2$ mediated inflammation and similar conditions utilizing compounds or compositions thereof are disclosed.

3 Claims, No Drawings

METHODS OF USING HYDROXY-, ALKOXY- AND BENZYLOXY-SUBSTITUTED PHOSPHOLIPIDS TO TREAT PHOSPHOLIPASE A₂-MEDIATED CONDITIONS AND TO ALLEVIATE PAIN

This is a division of application Ser. No. 367,926 filed June 15, 1989 now U.S. Pat. No. 5,030,733 which is a continuation-in-part application of prior application Ser. No. 076,966 filed July 23, 1987 now abandoned.

This invention relates to hydroxy-, alkoxy- and benzyloxy-substituted phospholipids. More particularly, this invention relates to alkylphospolipids of the formula:

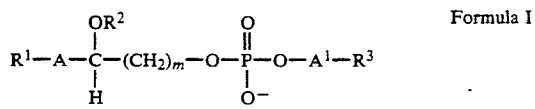

Formula I wherein $R^1$ is selected from the group consisting of hydrogen, substituted and unsubstituted phenyl radicals, and substituted and unsubstituted phenoxy radicals; $R^2$ is selected from the group consisting of hydrogen, alkyl radicals having up to 6 carbon atoms, inclusive, and phenyl-substituted and phenyl-unsubstituted benzyl radicals; $R^3$ is

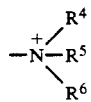

wherein $R^4$ is an alkyl radical having up to 6 carbon atoms, inclusive; $R^5$ and $R^6$ are independently alkyl radicals having up to 6 carbon atoms, inclusive, or, taken together with the nitrogen atom to which they are attached form a group of the formula

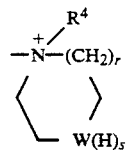

wherein r is 0 or 1; s is an integer which, depending upon the valency of W, has a value from 0 to 2 inclusive; and W is selected from the group consisting of carbon, oxygen, nitrogen and sulfur atoms, with the proviso that when W is other than a carbon atom, r is 1; A is a divalent radical of the formula $-C_nH_{2n}-$ wherein n is an integer having a value from 1 to 20, inclusive; m is an integer having a value of 3 or 4; $A^1$ is a bivalent radical of the formula $-C_pH_{2p}-$ wherein p is an integer having a value from 2 to 10, inclusive with the proviso that the sum of n and p does not exceed 25; the geometrical isomers, or optical antipodes thereof, which are useful as antiinflammatory agents alone or in combination with one or more adjuvants.

Preferred alkylphospolipids of this invention are compounds of the formula:

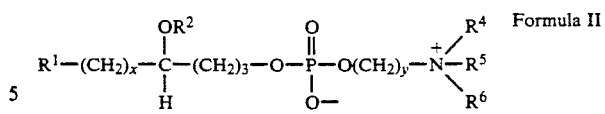

Formula II wherein $R^1$ is selected from the group consisting of hydrogen, substituted and unsubstituted phenyl radicals, and substituted and unsubstituted phenoxy radicals; $R^2$ is selected from the group consisting of hydrogen, alkyl radicals having up to 6 carbon atoms inclusive, and phenyl-substituted and phenyl-unsubstituted benzyl radicals; $R^4$ is an alkyl radical having up to 6 carbon atoms, inclusive; $R^5$ and $R^6$ are independently alkyl radicals having up to 6 carbon atoms, inclusive, or taken together with the nitrogen atom to which they are attached form a group of the formula

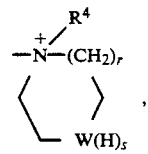

wherein r is 0 or 1; s is an integer which, depending upon the valency of W, has a value of from 0 to 2 inclusive; W is selected from the group consisting of carbon, oxygen, nitrogen and sulfur atoms, with the proviso that when W is other than a carbon atom, r is 1; x is an integer having a value from 1 to 20 inclusive; and y is an integer having a value from 2 to 5 inclusive; the geometrical isomers or optical antipodes thereof.

Subgeneric to the phospolipids of this invention are compounds wherein:

(a) $R^1$ is hydrogen;

(b) $R^1$ is a group of the formula

wherein a is an integer having a value from 0 to 2, inclusive, X is selected from the group consisting of alkyl radicals having 1 to 6, preferably 1 to 3, carbon atoms, inclusive; alkoxy radicals having 1 to 6, preferably 1 to 3, carbon atoms, inclusive; and halogen, preferably fluorine or chlorine, hydroxy, and trifluoromethyl radicals; wherein for each value of a, X may be the same or different;

(c) $R^1$ is a group of the formula

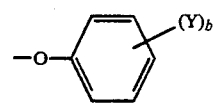

wherein b is an integer having a value from 0 to 2, inclusive, and Y is selected from the group consisting of alkyl radicals having 1 to 6, preferably 1 to 3 carbon atoms, inclusive; alkoxy radicals having 1 to 6, preferably 1 to 3 carbon atoms, inclusive, and halogen, preferably fluorine or chlorine, hydroxy, and trifluoromethyl radicals; wherein for each value of b, Y may be the same or different;

(d) $R^2$ is hydrogen;
(e) $R^2$ is an alkyl radical having up to 6 carbon atoms inclusive;
(f) $R^2$ is

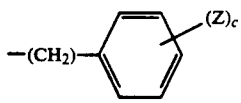

wherein c is an integer having a value of 0 or 1, and Z is an alkoxy radical having 1 to 6, preferably 1 to 3, carbon atoms, inclusive;
(g) $R^3$ is

wherein $R^4$, $R^5$ and $R^6$ are independently alkyl radicals having up to 6 carbon atoms, inclusive;
(h) $R^3$ is

wherein $R^4$ is an alkyl radical having up to 6 carbon atoms inclusive, and $R^5$ and $R^6$ together with the nitrogen atom to which they are attached form a group of the formula

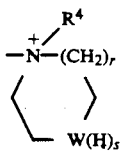

wherein W is selected from the group consisting of carbon, oxygen, sulfur and nitrogen atoms; s is an integer which, depending upon the valency of W, has a value from 0 to 2 inclusive; and r is 0 or 1.
(i) A is $-C_nH_{2n}-$ wherein n is an integer having a value from 1 to 20, inclusive, preferably from 7 to 17, inclusive; and
(j) A is $-(CH_2)_x-$ wherein x is an integer having a value from 1 to 20, inclusive, preferably from 7 to 17, inclusive;
(k) $A^1$ is $-C_pH_{2p}-$ wherein p is an integer having a value from 2 to 10, inclusive, preferably 2 to 5, most preferably 2;
(l) $A^1$ is $-(CH_2)_y-$ wherein y is an integer having a value from 2 to 5, inclusive.

As used herein the term "alkyl" refers to a straight or branched chain hydrocarbon radical containing no unsaturation, such as, for example methyl, ethyl, 1-propyl, 2-propyl, 1-butyl, 1-pentyl, 2-pentyl, 3-hexyl and the like; the term "alkoxy" refers to a monovalent substituent which consists of an alkyl group linked through an ether oxygen and having its free valence bond from the ether oxygen such as, for example methoxy, ethoxy, 1- and 2-propoxy, 1-butoxy, 1,2-dimethylethoxy, 1- and 2-pentoxy-, 3-hexoxy- and the like; and the term "benzyloxy" refers to a monovalent substituent which consists of a benzyl group linked through an ether oxygen and having its free valence bond from the ether oxygen; the term "halogen" refers to a member of the family of fluorine, chlorine, bromine or iodine; the term "phenoxy" refers to a monovalent substituent which consists of a phenyl group linked through an ether oxygen and having its free valence bond from the ether oxygen; the term "alkanol" refers to a compound formed by a combination of an alkyl group and a hydroxy radical such as, for example methanol, ethanol, 1- and 2-propanol, t-butanol, and the like; and the term "alkanoic acid" refers to a compound formed by combination of a carbonyl group with a hydrogen atom or alkyl group such as, for example, formic acid, acetic acid, propanoic acid, 2,2-dimethylacetic acid, hexanoic acid and the like.

The hydroxy-, alkoxy- and benzyloxy-substituted phospholipids of this invention are synthesized by the processes illustrated in Reaction Schemes A, B, C, D and E.

As shown by Reaction Scheme A, benzyloxy- or alkoxy-substituted alkanols of the formula

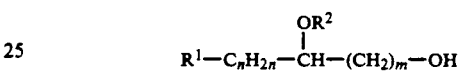

wherein $R^1$ is hydrogen, are produced by reacting an aldehyde 1 with an organometallic reagent 2 to produce an hydroxy-substituted 1-alkene 3 which is hydrated to an alkan-1-ol 5 via the corresponding alkoxy- or benzyloxy- substituted 1-alkene 4.

The reaction between the aldehyde 1 and the organometallic reagent 2 is generally conducted at a temperature of from about 0° C. to about 100° C. under anhydrous conditions in the presence of a inert organic solvent. Preferred reaction temperatures are subject to variation depending, in part, upon the reactivity of the particular organometallic reagent employed. Among the organometallic reagents there may be mentioned alkenylmagnesium halides and alkenyllithium compounds having a terminal double bond such as, for example, allylmagnesium bromide, allylmagnesium chloride, allylmagnesium iodide, 3-butenylmagnesium bromide, allyllithium, and the like. Allylmagnesium bromide is preferred. Suitable solvents for the reaction include ethers such as diethyl ether, dioxane, tetrahydrofuran, and the like; and, depending upon the stability of the organometallic reagent, aromatic hydrocarbons such as benzene, toluene, xylene, and the like. It should be noted, however, that a solvent selection is limited by the solubility of the particular organometallic reagent employed. Ethereal solvents, particularly tetrahydrofuran, are preferred.

The alkoxy- or benzyloxy substituted 1-alkenes 4 are produced by reacting the hydroxy-substituted 1-alkene 3 with an alkyl or benzyl halide (e.g. benzyl bromide, benzyl chloride, benzyl iodide, methyl bromide, ethyl bromide, and the like) under basic conditions. Among the bases which may be employed in this reaction are alkali metal hydrides, alkali metals, and the like, including, for example, sodium hydride, potassium hydride, sodium, and potassium. Sodium hydride is preferred. The reaction is generally conducted under anhydrous conditions in the presence of an ethereal and/or dipolar aprotic solvent such as tetrahydrofuran, dioxane, diethyl ether, bis(2-methoxyethyl)ether, 1,2-dimethoxyethane, dimethylformamide, dimethylacetamide, dimethylsulfoxide, and hexamethylphosphoramide. Preferred solvents include tetrahydrofuran, dimethylformamide, and mixtures thereof.

Conversion of the alkoxy- or benzyloxy-substituted 1-alkene 4 to the corresponding 1-alkanol 5 may be accomplished by reacting the 1-alkene 4 with an appropriate hydroborating agent, followed by oxidation of the resulting borane to an alcohol 5. Among the hydroborating agents there may be mentioned 9-borabicyclo[3.3.1]nonane, diborane, and dialkylboranes such as dimethyl borane, diethyl borane, and the like. 9-Borabicyclo[3.3.1]nonane is preferred. Depending upon the activity of the hydroborating agent, the reaction is conducted under an inert atmosphere. For example, when the hydroborating agent is 9-borabicyclo[3.3.1]nonane, it is recommended that the reaction be conducted under nitrogen. The hydroboration of the 1-alkene 4 is conducted at a temperature of from about 0° C. about 50° C., preferably from about 0° C. to about 20° C., in the presence of an inert organic solvent. Suitable solvents include ethereal solvents, aromatic hydrocarbons, halocarbons, and the like, such as, for example, tetrahydrofuran, diethylether, dioxane, benzene, toluene, xylene, dichloromethane, 1,1- and 1,2-dichloromethane, 1,1- and 1,2-dichloroethene and the like. Ethereal solvents, particularly tetrahydrofuran are preferred. Oxidation of the borane is conventionally accomplished by treatment with alkaline hydrogen peroxide at a temperature of from about 0° C. to about 100° C. Preferred temperatures for the oxidation range from about 20° C. to about 50° C.

As illustrated by Reaction Scheme B, benzyloxy- or alkoxy-substituted alkanols of the formula

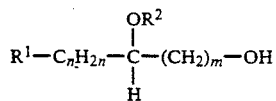

wherein $R^1$ is a phenyl or phenoxy group, may be prepared by treating a 1-alkene 6 with ozone followed by an appropriate organometallic reagent to produce an hydroxy substituted 1-alkene. Conversion of the hydroxy-substituted 1-alkene 3 to the corresponding alkoxy- or benzyloxy-substituted 1-alkene 4, followed by hydration of the terminal double bond provides an alkoxy- or benzyloxy- substituted alkan-1-ol 5. Treatment of the 1-alkene 6 with ozone is generally conducted at temperatures of from about −70° C. to about 0° C. in the presence of an anhydrous organic solvent. Suitable solvents include aromatic hydrocarbons and ethereal solvents such as benzene, toluene, xylene, diethyl ether, tetrahydrofuran dioxane and the like. In general, toluene is the preferred solvent. Appropriate organometallic reagents are as described in the context of Reaction Scheme A. As organometallic reagents, Grignard reagents, particularly allylmagnesium bromide, are preferred. In general, the organometallic reaction is conducted at a temperature of from about 0° C. to about 100° C., preferably from about 0° C. to about 65° C.

The hydroxy substituted alkene 3 is treated with an alkyl halide to produce a benzyloxy- or alkoxy-substituted alkene 4, which is converted to an alkan-1-ol, 5 via the corresponding borane, all as previously described in the context of Reaction Scheme A.

Reaction Scheme C illustrates an alternative synthesis for the production of benzyloxy- or alkoxy-substituted alkan-1-ols of the formula

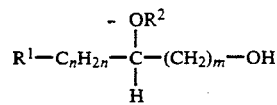

wherein $R^1$ is hydrogen. As shown by this scheme, an alkyl metal halide 7 is reacted with a (tetrahydro-2H-pyran-2-yl)oxy-substituted aldehyde 8 to produce an hydroxy-substituted alkane 9, which is thereafter converted to the corresponding alkoxy or benzyloxy-substituted alkane 10 and subsequently cleaved to an alkan-1-ol 5.

The reaction of the alkyl metal halide 7 and aldehyde 8 is typically conducted under anhydrous conditions at a temperature of from about 0° C. to about 100° C. in the presence of an inert organic solvent. Preferred reaction temperatures range from about 0° C. to about 35° C. Among the appropriate solvents there may be mentioned ethereal solvents such as dioxane, diethyl ether, tetrahydrofuran and the like. Diethyl ether is preferred. Conversion of the hydroxy- substituted alkane 9 to the corresponding benzyloxy- or alkoxy- substituted alkan-1-ol 5 may be accomplished by treatment with an alkyl or benzyl halide followed by cleavage of the (tetrahydro-2H-pyran-1-yl)oxy group of the alkoxy or benzyloxy- substituted alkane 10. Treatment of the hydroxy-substituted alkane 9 with an alkyl or benzyl halide is conveniently accomplished under basic conditions at a temperature of from about 0° C. to about 100° C. in the presence of an inert organic solvent. Suitable solvents include ethereal solvents such as diethyl ether, dioxane, 1,2-dimethoxyethane, tetrahydrofuran and the like, as well as polar aprotic solvents such as dimethylformamide, dimethylacetamide, dimethylsulfoxide, hexamethylphosphoramide, and the like. Tetrahydrofuran or dimethylformamide is preferred. Suitable bases include alkali metal hydrides such as sodium hydride, potassium hydride, and the like, and alkali metals such as sodium and potassium. Sodium hydride is preferred. Optionally, the reaction is conducted in the presence of a promoter such as, for example, tetrabutylammonium iodide.

Cleavage of the (tetrahydro-2H-pyran-1-yl)oxy group is achieved by treatment of the alkoxy- or benzyloxy-substituted alkane 10 with an appropriate acid (e.g. hydrochloric acid, sulfuric acid, hydrobromic acid, and the like), preferably hydrochloric acid), at a temperature of from about 0 to about 100° C., preferably from about 25 to about 50, in the presence of a suitable organic solvent. Suitable solvents include alkanols such as, for example, methanol, ethanol, propanol, and the like. Ethanol is preferred.

As shown by Reaction Scheme D, Formula I compounds wherein $A^1$ is —$C_2H_4$— may be prepared by phosphorylating an alkoxy- or benzyloxy-substituted-alkan-1-ol 5 with 2-chloro-2-oxo-1,3,2-dioxaphospholane 11, and reacting the resultant cyclic triester 12 with a tertiary amine 13 to form an alkylphospholipid 14.

The phosphorylation of the substituted alkan-1-ol 5 (i.e. an alkanol of the formula

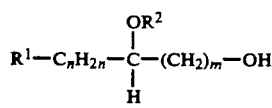

wherein $R^1$ is hydrogen, a phenyl group, or a phenoxy group; see Reaction Schemes A, B and C) by reaction with 2-chloro-2-oxo-1,3,2-dioxaphospholane 16 is generally conducted under anhydrous conditions at a temperature of from about 0° to about 100° C. in the presence of an inert organic solvent. Preferred temperatures for the phosphorylation reaction range from about 0° to about 30° C. Suitable solvents include ethereal solvents such as, for example, dimethyl ether, tetrahydrofuran, dioxane, dimethoxyethane and the like, aromatic hydrocarbons such as benzene, toluene, xylene and the like, halocarbons such as chloroform, methylene chloride; and the like, and mixtures thereof. The reaction is optionally conducted in the presence of an acid acceptor. Among the suitable acid acceptors there may be mentioned organic bases, such as, for example tertiary and heterocyclic amines (e.g., trimethyl, tripropyl, triethyl amine, pyridine, picoline, lutidine, collidine and the like). Mixtures of (a) triethylamine or pyridine and (b) tetrahydrofuran or toluene are preferred.

The conversion of the cyclic triester 12 to a phospholipid 14, is typically accomplished under anhydrous conditions in the presence of an inert organic solvent at a temperature of from about 0° C. to about 100° C., preferably from about 60° C. to about 80° C. In addition to the ethereal and halocarbon solvents mentioned supra in connection with the phosphorylation reaction, suitable solvents include polar aprotic solvents such as dimethylformamide, dimethylacetamide, hexamethylphosphoramide and the like, and acetonitrile. Acetonitrile is preferred. Selection of the tertiary amine 13 is determined in part by the quaternary group desired in the resultant alkylphospholipid 14. Among the tertiary amines 13 are aliphatic amines such as, for example, trimethylamine, triethylamine, N,N-dimethylethyl amine and the like; and heterocyclic amines such as, for example, N-alkyl pyrrolidines, piperidines, piperazines, morpholines, thiomorpholines and the like, such as, for example, N-methylpyrrolidine, N-ethylpyrrolidine, N-methylpiperidine, N-methylpiperazine, 1,4-dimethylpiperazine, 4-methylmorpholine, 4-ethylmorpholine, and the like. Trimethylamine and N-methylpyrrolidine are preferred.

Benzyloxy-substituted alkylphospholipids 14 are converted to the corresponding hydroxy-substituted alkylphospholipids 15 by hydrogenation in the presence of an appropriate catalyst. The hydrogenation reaction is conducted at a temperature from about 15° C. to about 100° C. and a hydrogen gas pressure of from about 1 atmosphere to about 10 atmospheres in an appropriate solvent. Hydrogenation temperatures of from about 20° C. to about 30° C. and hydrogen gas pressures of from about 1 atmosphere to about 4 atmospheres are preferred. Among the suitable solvents for the hydrogenation reaction are alkanols, including methanol, ethanol, 2-propanol, and the like; alkanoic acids, including formic acid, acetic acid and propanonic acid and the like; and the alkyl esters of the aforementioned alkanoic acids. Preferred solvents are ethanol, mixtures of ethanol and acetic acid, and mixtures of ethanol and ethyl acetate. Catalysts include nobel metals (e.g. palladium, platinum and rhodium). 5% palladium on carbon is preferred.

Alternatively, as shown in Reaction Scheme E, compounds wherein $A^1$ is a bivalent radical of the formula $-C_pH_{2p}-$ wherein p is as previously defined may be prepared by reacting an alkoxy- or benzyloxy substituted alkan-1-ol 5 with an appropriate phosphorylating agent 16, followed by quaternization of the resultant phosphate diester 17 to an alkylphospholipid 18. Included among the phosphorylating agents suitable for use herein are haloalkylphosphorodichloridates such as 2-bromoethylphosphorodichloridate, 2-chloroethylphosphorodichloridate, 2-iodoethylphosphorodichloridate, 4-bromobutylphosphorodichloridate, 6-bromohexylphosphodichloridate and the like. The phosphorylation reaction is generally conducted under anhydrous conditions in the presence of a basic organic solvent. Basic organic solvents include aliphatic and heterocyclic tertiary amines such as trimethylamine, triethylamine, pyridine, and the like. The reaction may be conducted in the presence of an appropriate co-solvent. Suitable co-solvents include etheral solvents such as diethyl ether, dioxane, tetrahydrofuran and the like; aromatic hydrocarbons such as benzene, toluene, xylene and the like; and halocarbons such as dichloroethane, chloroform methylene chloride, and the like. Mixtures of triethylamine or pyridine and diethyl ether are preferred. The phosphorylation reaction may be conducted at a temperature of from about 0° C. to about 25° C. Preferred reaction temperatures are subject to variation depending upon the reactivity of the particular reactants employed.

Quaternization of the phosphate diester 17 to the alkylphospholipid 18 is conveniently accomplished under hydrous or anhydrous conditions utilizing the tertiary amines previously described in Reaction Scheme D. Trimethylamine and N-methylpyrrolidine are preferred. The quaternization reaction may be conducted at a temperature of from about 20° C. to about 100° C., in the presence of an appropriate solvent. Among the suitable solvents there may be mentioned polar aprotic solvents such as dimethylacetamide, dimethylformamide, hexamethyl phosphoramide, dimethyl sulfoxide and the like; halocarbons such as dichloromethane, chloroform, dichloroethane and the like; ethereal solvents such as diethyl ether, dioxane, tetrahydrofuran and the like, alkanols such as methanol, ethanol, 1- and 2-propanol and the like; acetonitrile and the like; and mixtures thereof. Acetonitrile and mixtures of acetonitrile and isopropanol are preferred. Desirably, water is present as a co-solvent. Preferably the reaction is conducted at the reflux temperature of the solvent medium and the resultant adduct is treated with silver carbonate to generate the desired product 18. Hydrogenation of the benzyloxy-substituted phospholipid 18, under conditions as previously described, forms the corresponding hydroxy-substituted alkylphospholipid 19.

It is a purpose of this invention to provide a method of treating and/or preventing phospholipase $A_2$ mediated inflammatory and related conditions by inhibiting the lipolytic ability of phospholipase $A_2$. Phospholipase $A_2$, an enzyme involved in phospholipid degradation as well as various metabolic regulatory processes, has been linked to the initiation of the arachidonic acid cascade. Derivatives produced by the various enzymes of the cascade include prostaglandins, eicosatetraenoic acids, eicosatrienoic acids, thromboxanes and leukotrienes.

The presence of several of these hydroxylated derivatives is associated with diseases or conditions which include systemic inflammation, ocular inflammation, dermal inflammation, rheumatoid arthritis, erythema and allergic responses (e.g. asthma, hay fever, etc.). Blocking the production of such derivatives as a means of suppressing inflammatory conditions in animal models is disclosed, for example, by R. J. Flower, in Nature, Vol. 320, p. 20, Mar. 6, 1986.

The phospholipase $A_2$ inhibiting ability of the compounds of this invention was evaluated by means of a modification of the assay procedure disclosed by H. S., Hendrickson, E. K., and Dybvig, R. H. in Chiral Synthesis of a Ditholester Analog of Phosphatidylcholine as a Substrate for the Assay of Phospholipase $A_2$, *Journal of Lipid Research*, Vol. 24, pp 1532-1537 (1983) (hereinafter "Hendrickson et al."). The substrate employed in the modified assay, was 1,2-bis(decanoylthio)-1,2-dideoxyglycerol-3-phosphocholine (hereinafter "Thio Pc Substrate"). The enzyme utilized in the procedure was phospholipase $A_2$ isolated from rat peritoneum as follows:

Male Wistar rats weighing 200-300 g a piece were injected interperitoneally at a dosage of 50 ml/kg of body weight (20 g of casein as the sodium salt diluted to 500 ml in distilled water). After a period of 18-24 hours the animals were sacrificed. Thereafter, each animal was injected interperitoneally with 30 ml of an isotonic salt solution to which sodium heparin was added prior to use at a concentration of 5 units/ml. Enzyme-containing exudate was aspirated through an abdominal incision. Separation of the enzyme from the exudate was accomplished by centrifugation.

Pursuant to the assay procedure, Thio Pc Substrate was apportioned into 1.25 mg aliquots. To each aliquot was added 4 ml of 160 mM tris hydrogen chloride buffer (pH 7.5) containing 2mM of calcium chloride and 2mM of sodium taurocholate. The resulting dispersions were vortexed at room temperature to clear solutions. Inhibition activity of the alkylphospholipids of this invention was determined utilizing spectrophotometric samples prepared by the addition of 5 ul of 4,4'dithiopyridine and 395 ml of buffered Thio Pc substrate to a perincubated dispersion of 50 ul of alkylphospholipid (appropriately diluted in buffer) in 50 ul of enzyme (appropriately diluted in buffer). Absorbence at (0.5 full scale) was recorded at a chart speed of 2 cm/min on a Gilford Model 250 Spectrophotometer.

The percentage of phospholipase $A_2$ inhibition was calculated by means of the following formula:

$$\% PLA_2 \text{ Inhibition} = 100 - \frac{\text{Inhibitor Slope}}{\text{Control Slope}} \times 100$$

wherein "inhibitor slope" is the slope of the spectrophotometric curve obtained for a given alkylphospholipid-containing sample and "control slope" is the slope of the spectrophotometric curve obtained for an otherwise identical sample lacing an inhibitor.

The phospholipase $A_2$-inhibiting ability of several of the compounds of this invention are provided in the following Table:

TABLE 1

| Compound | % $PLA_2$ Inhibition |
| --- | --- |
| 4-hydroxy-N,N,N-trimethyl-9-phenylmethoxy-3,5-dioxa-4-phosphatetracosan-1-aminium, 4-oxide, hydroxide, inner salt monohydrate | 41.8% @ $1.0 \times 10^{-4}$M |
| 4,9-dihydroxy-N,N,N-trimethyl-3,5-dioxa-4-phosphatetracosan-1-aminium, 4-oxide, hydroxide, inner salt sesquihydrate | 45.6% @ $1.0 \times 10^{-4}$M |
| 4-hydroxy-N,N,N-trimethyl-9-phenylmethoxy-3,5-dioxa-4-phosphahexacosan-1-aminium, 4-oxide, hydroxide, inner salt monohydrate | *$IC_{50} = 8.4 \times 10^{-5}$M |
| 4,9-dihydroxy-N,N,N-trimethyl-3,5-dioxa-4-phosphapentacosan-1-aminium, 4-oxide, hydroxide, inner salt monohydrate | *$IC_{50} = 9.5 \times 10^{-5}$M |
| Quinacrine | *$IC_{50} = 3.1 \times 10^{-5}$M |

*wherein $IC_{50}$ is that concentration of inhibitor which reduces enzymatic activity by 50%

Thus, the products of the present invention are useful to inhibit phospholipase $A_2$ in a mammalian system whenever it is deemed necessary or desirable. They are especially useful in treating symptoms or conditions resulting from excessive stimulation of the arachidonic acid cascade during certain disease processes or conditions such as inflammation, erythema and allergic responses.

Although the precise mechanisms of the disease processes or conditions which stimulate the arachidonic acid cascade are not clearly understood, the essential prerequisite appears to be an enhanced activity of the phospholipases which provide arachidonate to the series of biochemical reactions designated as the arachidonic acid cascade. The method of this invention is simply to block the action of the phospholipases and cut off the flow of arachidonate into the cascade, irrespective of the stimuli which may be present. This can be accomplished by compounds of the present invention. Thus, the method of this invention is suitable for treating a myriad of seemingly unrelated diseases whose common element is the stimulation of the arachidonic cascade.

The phospholipids of the invention are effective in the treatment of phospholipase $A_2$ mediated inflammatory conditions when administered orally, peritoneally, intravenously or topically to a subject requiring such treatment at a dose of from about 0.1 to about 60 mg/kg of body weight per day.

It is to be understood that specific dosage regimens should be adjusted according to the individual need of a particular subject and the professional judgment of the person administering or supervising the administration of the compounds of this invention. Individual requirements will depend on factors which include the particular phospholipase $A_2$ mediated inflammatory condition being treated and its severity; the age, weight, physical condition, and sex of the subject; as well as the particular administrative method(s) employed.

The compounds of the present invention are also useful as analgesic agents due to their ability to alleviate pain in mammals. The activity of the compounds is demonstrated in the phenyl-para-quinone writhing assay in mice, a standard assay for analgesia [Proc. Soc. Exptl. Biol. Med., 95, 729 (1957)]. Presented in Table 2 is the analgesic effect of some of the compounds of the invention expressed as either the subcutaneous dose at which 50% of the phenyl-para-quinone induced writhing is inhibited in the animals, i.e., the $ED_{50}$ value, or at the % decrease in writhing at a give dose.

TABLE 2

| Compound | Analgesic PQW % Inhibition of Writhing at 20 mg/kg, s.c. |
|---|---|
| 4-hydroxy-N,N,N-trimethyl-9-phenylmethoxy-3,5-dioxa-4-phosphaoctadecan-1-aminium, 4-oxide, hydroxide, inner salt monohydrate | 83% |
| 4-hydroxy-N,N,N-trimethyl-9-phenylmethoxy-3,5-dioxa-4-phosphatetracosan-1-aminium, 4-oxide, hydroxide, inner salt monohydrate | 36% |
| 4,9-dihydroxy-N,N,N-trimethyl-3,5-dioxa-18-phenoxy-4-phosphaoctadecan-1-aminium, 4-oxide, hydroxide, inner salt monohydrate | 48% |
| 4,9-dihydroxy-N-methyl-3,5-dioxa-4-phosphatetracosan-1-pyrrolidinium, 4-oxide, hydroxide, inner salt 3.5 hydrate | 62% |
| Propoxyphene (reference compound) | 50% at 3.9 mg/kg, s.c. |

The analgesic relief of pain is achieved when the compounds of the invention are administered to a subject requiring such treatment at an effective oral, parenteral or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are exemplary only and that they do not, to any extent, limit the scope or practice of the invention.

For the purpose of oral therapeutic administration, the aforesaid compounds may be incorporated with excipients, diluents and/or carriers and used in the form of tablets, troches, capsules, elixirs, suspensions, syrups, wafers, chewing gums and the like. These preparations should contain at least 0.5% of active compound, but may be varied depending upon the particular form and may conveniently be between 4% and 70% of the weight of the unit. The amount of active compound is such that a suitable dosage will be obtained. Preferred compositions and preparations according to the present invention are prepared so that an oral dosage form contains between 1.0 and 300 milligrams of the active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral or topical therapeutic administration, the active compounds of the invention may be incorporated into a solution, suspension, ointment or cream. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral or topical dosage unit contains between 0.5 and 100 milligrams of active compound.

The solutions or suspensions for topical or parenteral administration may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules or disposable syringes; the topical preparation may be enclosed in multiple dose vials or dropping bottles, made of glass or plastic.

Included among the compounds of this invention are:
4-hydroxy-N,N,N-trimethyl-9-methoxy-3,5-dioxa-18-phenoxy-4-phosphaoctadecan-1-aminium, 4-oxide, hydroxide inner salt;
5-hydroxy-N,N,N-trimethyl-10-phenylmethoxy-4,6-dioxa-18-phenyl-5-phosphanonadecan-1-aminium,5-oxide, hydroxide inner salt;
5,10-dihydroxy-N,N,N-trimethyl-4,6-dioxa-5-phosphanonadecan-1-aminium, 5-oxide, hydroxide inner salt;
6,11-dihydroxy-N,N,N-trimethyl-5,7-dioxa-6-phosphatetracoden-1-aminium, 6-oxide, hydroxide, inner salt;
4-hydroxy-1-methyl-3,5-dioxa-9-phenylmethoxy-4-phosphaoctadecan-1-piperidium, 4-oxide, hydroxide, inner salt;
4,9-dihydroxy-N,N,N-trimethyl-3,5-dioxa-4-phosphatridecan-1-aminium, 4-oxide, hydroxide, inner salt;
4-hydroxy-N,N,N-trimethyl-9-methoxy-N,N,N-trimethyl-3,5-dioxa-4-phosphatridecan-1-aminium, 4-oxide, hydroxide, inner salt;
4-hydroxy-N,N,N-trimethyl-9-phenylmethoxy-3,5-dioxa-4-phosphatridecan-1-aminium, 4-oxide, hydroxide, inner salt;
4-hydroxy-N,N,N-trimethyl-9-(4-methylphenyl)methoxy-3,5-dioxa-4-phosphatridecan-1-aminium, 4-oxide, hydroxide, inner salt;
4-hydroxy-N,N,N-trimethyl-9-(4-chlorophenyl)methoxy-3,5-dioxa-4-phosphatridecan-1-aminium, 4-oxide, hydroxide, inner salt;
4,9-dihydroxy-N-methyl-3,5-dioxa-4-phosphatridecan-1pyrrolidinium, 4-oxide, hydroxide, inner salt;
4,9-dihydroxy-N-methyl-3,5-dioxa-4-phosphatridecan-1-piperidium, 4-oxide, hydroxide, inner salt;

4,9-dihydroxy-N-methyl-N'-phenyl-3,5-dioxa-4-phosphatridecan-1-piperazinium, 4-oxide, hydroxide, inner salt;

4,9-dihydroxy-N-methyl-3,5-dioxa-4-phosphatridecan-1-(4-morpholinium), 4-oxide, hydroxide, inner salt;

4,9-dihydroxy-N-methyl-3,5-dioxan-4-phosphatridecan-1-(4-thiomorpholinium), 4-oxide, hydroxide, inner salt;

4,10-dihydroxy-N,N,N-trimethyl-3,5-dioxa-4-phosphatetradecan-1-aminium, 4-oxide, hydroxide, inner salt;

4-hydroxy-N,N,N-trimethyl-10-ethoxy-N,N,N-trimethyl-3,5-dioxa-4-phosphatetradecan-1-aminium, 4-oxide, hydroxide, inner salt;

4-hydroxy-N,N,N-trimethyl-10-phenylmethoxy-3,5-dioxa-4-phosphatetradecan-1-aminium, 4-oxide, hydroxide, inner salt;

4-hydroxy-N,N,N-trimethyl-10-(4-methoxyphenyl)methoxy-3,5-dioxa-4-phosphatetradecan-1-aminium, 4-oxide, hydroxide, inner salt;

4-hydroxy-N,N,N-trimethyl-10-[4-(trifluoromethyl)-phenyl]methoxy-3,5-dioxa-4-phosphatetradecan-1-aminium, 4-oxide, hydroxide, inner salt;

4,10-dihydroxy-N-methyl-3,5-dioxa-4-phosphatetradecan-1-pyrrolidinium, 4-oxide, hydroxide, inner salt;

4,9-dihydroxy-N,N,N-trimethyl-3,5-dioxa-13-phenyl-4-phosphatridecan-1-aminium, 4-oxide, hydroxide, inner salt;

4,9-dihydroxy-N,N,N-trimethyl-3,5-dioxa-13-phenoxy-4-phosphatridecan-1-aminium, 4-oxide, hydroxide, inner salt;

4,9-dihydroxy-N-methyl-3,5-dioxa-13-phenyl-4-phosphatridecan-1-pyrrolidinium, 4-oxide, hydroxide, inner salt;

4,10-dihydroxy-N,N,N-trimethyl-3,5-dioxa-14-phenyl-4-phosphatetradecan-1-aminium, 4-oxide, hydroxide, inner salt;

6,11-dihydroxy-N,N,N-trimethyl-5,7-dioxa-6-phosphaheptadecan-1-aminium, 6-oxide, hydroxide, inner salt;

6-hydroxy-N,N,N-trimethyl-11-phenylmethyl-4,6-dioxa-6-phosphaheptadecan-1-aminium, 6-oxide, hydroxide, inner salt;

6,11-dihydroxy-N-methyl-5,7-dioxa-6-phosphaheptadecan-1-pyrrolidinium, 6-oxide, hydroxide, inner salt;

6-hydroxy-11-methoxy-N-methyl-5,7-dioxa-6-phosphaheptadecan-1-pyrrolidinium, 6-oxide, hydroxide, inner salt;

6-hydroxy-11-methoxyphenyl-N-methyl-5,7-dioxa-17-phenyl-6-phosphaheptadecan-1-pyrrolidinium, 6-oxide, hydroxide, inner salt;

5,11-dihydroxy-N,N,N-trimethyl-4,6-dioxa-5-phosphadocosan-1-aminium, 5-oxide, hydroxide, inner salt;

5,11-dihydroxy-N,N,N-trimethyl-4,6-dioxa-22-phenyl-5-phosphadocosan-1-aminium, 5-oxide, hydroxide, inner salt;

5-hydroxy-N,N,N-trimethyl-11-phenylmethoxy-4,6-dioxa-5-phosphadocosan-1-aminium, 5-oxide, hydroxide, inner salt;

5-hydroxy-N-methyl-11-phenylmethoxy-4,6-dioxa-22-phenyl-5-phosphadocosan-1-aminium, 5-oxide, hydroxide, inner salt;

5-hydroxy-N-methyl-11-(2,4-difluorophenyl)methoxy-4,6-dioxa-5-phosphadocosan-1-piperidium, 5-oxide, hydroxide, inner salt;

4,9-dihydroxy-N,N,N-trimethyl-3,5-dioxa-4-phosphaheptacosan-1-aminium, 4-oxide, hydroxide, inner salt;

4,9-dihydroxy-N,N,N-trimethyl-3,5-dioxa-28-phenyl-4-phosphaheptacosan-1-aminium, 4-oxide, hydroxide, inner salt; and 8,13-dihydroxy-N,N,N-trimethyl-7,9-dioxa-8-phosphahentriacontan-1-aminium, 8-oxide, hydroxide, inner salt.

EXAMPLES

The following Examples are for illustrative purposes only and are not to be construed as limiting the invention. All temperatures are given in degrees centigrade (°C). With the exception of yields which are calculated on a molar basis, all percentages are by volume, unless otherwise noted.

EXAMPLE 1

4-Hydroxy-N,N,N-trimethyl-9-phenylmethoxy-3,5-dioxa-4-phosphaoctadecan-1-aminium, 4-oxide, hydroxide, inner salt monohydrate Step 1

A solution of 10 g of 1-tridecen-4-ol in 100 ml of tetrahydrofuran was added, dropwise, under nitrogen to hexane-washed sodium hydride (from 3.15 g of a 50% oil dispersion). The mixture was stirred at 50° and a solution of 6.6 ml of benzyl bromide in 50 ml of dimethylformamide was added, dropwise. The reaction mixture was refluxed for 3 hrs., cooled, quenched by the addition of 25 ml of water, and concentrated. The concentrate was extracted three times with 100 ml aliquots of hexane/diethyl ether (2:1 by volume). The combined extracts were washed with 100 ml of water and 100 ml of a saturated aqueous solution of sodium chloride, dried over anhydrous magnesium sulfate and concentrated. Purification of the concentrate by flash chromatography on silica gel utilizing 1% diethyl ether/hexane as an eluent yielded 11.77 g (81%) of 4-benzyloxy-1-tridecene as an oil.

ANALYSIS: Calculated for $C_{20}H_{32}O$: 83.27%C; 11.18%H; Found: 83.46%C; 11.21%H.

Step 2

A solution of 9.3 g of 4-benzyloxy-1-tridecene in 40 ml of tetrahydrofuran was added, dropwise, under nitrogen, to 70.4 ml of 9-borabicyclo[3.3.1]nonane (0.5M solution in hexane). The reaction mixture was stirred at room temperature for 3 hrs. and quenched by the sequential addition of 18 ml of ethanol, 6 ml of 6N sodium hydroxide, and 12 ml of 30% hydrogen peroxide. The reaction mixture was heated at 50° for 2 hrs. and then allowed to stand at ambient temperature overnight. Upon standing the mixture separated into aqueous and organic phases. The aqueous phase was saturated with potassium carbonate and the organic phase was separated, washed with 30 ml of a 10% aqueous solution of sodium sulfite and 30 ml of a saturated aqueous solution of sodium chloride, dried over anhydrous potassium carbonate, and concentrated. The residue was taken up in 20% diethyl ether/hexane, filtered, and concentrated to an oil. Flash chromatography of the oil on silica gel using hexane diethyl ether (2:1 by volume) as the eluent yielded 7.7 g (80%) of 4-benzyloxytridecan-1-ol as an oil.

ANALYSIS: Calculated for $C_{20}H_{34}O_2$: 78.38%C; 11.18%H; Found: 76.65%C; 11.45%H.

Step 3

To a stirred solution of 18.2 g of 2-bromoethyl phosphorodichloridate in 400 ml of diethyl ether, cooled to 0°, was added, dropwise, in the following order, 30 ml of pyridine, and a solution of 11.48 g of 4-benzyloxytridecan-1-ol in 400 ml of diethyl ether. Upon the completion of the addition, the reaction mixture was stirred for 30 minutes at 0°, warmed to room temperature, diluted with water and acidified to a pH of 2 by the addition of 6N hydrochloric acid. Upon standing the reaction mixture separated into aqueous and organic layers. The organic layer was washed with 100 ml of a saturated solution of sodium chloride, dried over anhydrous magnesium sulfate, and concentrated. The concentrate was purified by high pressure liquid chromatography- utilizing 6% methanol/dichloromethane as the eluent to give 11.48 g (62%) of 2-bromoethyl 4-benzyloxytridecan-1-yl phosphate as a solid.

ANALYSIS: Calculated for $C_{22}H_{38}PO_5Br$: 53.55%C; 7.76%H; 6.28%P; Found: 53.30%C; 7.52%H; 6.41%P.

Step 4

To a solution of 10.22 g of 2-bromoethyl 4-benzyloxytridecan-1-yl phosphate in 92 ml of trichloromethane was a dropwise in the following order, 149 ml of isopropyl alcohol, 149 ml of acetonitrile, and 290 ml of a 33% aqueous solution of trimethylamine. The reaction mixture was stirred at 55° for 20 hrs., cooled and concentrated. The residue was taken up in 250 ml of methanol, refluxed with 8 g of silver carbonate for 2 hrs, filtered and concentrated. The concentrate was purified by means of flash chromatography using as successive eluents chloroform/methanol (9:1 by volume), chloroform/methanol (4:1 by volume), and chloroform/methanol/water (120:30:4 by volume).

Azeotroping with toluene followed by standing overnight yielded 4.32 g (52%) of 4-hydroxy-N,N,N-trimethyl-9-phenylmethoxy-3,5-dioxa-4-phosphaoctadecan-1-aminium, 4-oxide, hydroxide, inner salt monohydrate.

ANALYSIS: Calculated for $C_{25}H_{46}NO_5P.H_2O$: 61.32%C; 9.88%H; 2.86%N; 6.33%P; Found: 61.07%C; 9.79%H; 2.84%N; 6.24%P.

EXAMPLE 2

4,9-Dihydroxy-N,N,N-trimethyl-3,5-dioxa-4-phosphaoctadecan-1-aminium, 4-oxide, hydroxide, inner salt trihydrate A mixture of 3.26 g of 4-hydroxy-N,N,N-trimethyl-7-phenylmethoxy-3,5-dioxa-4-phosphaoctadecan-1-aminium, 4-oxide, hydroxide, inner salt monohydrate (prepared as in Example 1), 100 ml of ethanol, 50 ml of ethyl acetate and 0.5 g of 5% palladium on carbon was hydrogenated for 13 hrs. at 50 psi. The reaction mixture was filtered and concentrated. The concentrate was purified by flash chromatography on silica gel using as successive eluents chloroform/methanol (9:1 by volume) and chloroform/methanol/water (120:30:4 by volume) to yield 0.96 g (35%) of 4,9-dihydroxy-N,N,N-trimethyl-3,5-dioxa-4-phosphaoctadecan-1-aminium, 4-oxide, hydroxide, inner salt trihydrate, mp 235–239°.

ANALYSIS Calculated for $C_{18}H_{40}NO_5P$ $3H_2O$: 49.64%C; 10.65%H; 3.20%N; 7.11%P; Found: 49.31%C; 10.12%H; 3.15%N; 6.75%P.

EXAMPLE 3

4-Hydroxy-1-methyl-3,5-dioxa-9-phenylmethoxy-4-phosphaoctadecan-1-pyrrolidinium, 4-oxide, hydroxide, inner salt tetrahydrate To a stirred, anhydrous solution of 6 g of 4-benzyloxytridecan-1-ol (prepared as in Step 2 of Example 1) in 3.3 ml of triethylamine and 200 ml of toluene was added dropwise, under nitrogen, 2.8 g of 2-chloro-2-oxo-1,3,2-dioxaphospholane. The reaction mixture was stirred at ambient temperature overnight, filtered and concentrated. The residue was dissolved in 115 ml of acetonitrile, combined with 5.1 g of N-methylpyrrolidine, refluxed for 40 hrs. and concentrated. The residue was purified by flash chromatography using as successive eluents chloroform/methanol (9:1 by volume) followed by chloroform/methanol/water (120:30:4 by volume) to yield 5.8 g (59%) of 4-hydroxy-1-methyl-3,5-dioxa-9-phenylmethoxy-4-phosphaoctadecan-1-pyrrolidinium, 4-oxide, hydroxide, inner salt tetrahydrate as a gum.

ANALYSIS: Calculated for $C_{27}H_{48}NO_5P$ $4H_2O$: 56.92%C; 9.91%H; 2.46%N; 5.43%P; Found: 57.40%C; 9.66%H; 2.39%N; 5.71%P;

EXAMPLE 4

4-Hydroxy-N,N,N-trimethyl-9-phenylmethoxy.3,5-dioxa-4-phosphatetracosan-1-aminium, 4-oxide, hydroxide, inner salt monohydrate

Step 1

To 93 ml of a solution of allylmagnesium bromide in diethylether (1.0 M) was added, dropwise, a solution of 26 g of hexadecanal in 120 ml of tetrahydrofuran while maintaining a temperature of less than 30°. Following the addition, the reaction mixture was stirred for 16 hours at ambient temperature, poured onto ice, and diluted with a saturated aqueous ammonium chloride. Evaporation of the organic phase yielded a slurry. The slurry was acidified to a pH of 2 by the addition of 9 M sulfuric acid, and extracted with ethyl ether. The extract was washed with water until neutral, with a saturated solution of sodium chloride, dried over anhydrous sodium sulfate, and evaporated to give 28 g of an oil. High pressure liquid chromatography of the oil yielded 13.3 g of 1-nonadecen-4-ol as a wax, mp 37°–39.5°.

ANALYSIS: Calculated for $C_{19}H_{38}O$: 80.78%C; 13.56%H; Found: 80.88%C; 13.52%H;

Step 2

To a solution of 11.0 g of 1-nonadecen-4-ol in 60 ml of dimethylformamide was added hexane-washed sodium hydride (from 2.34 g of a 50% oil dispersion). The reaction mixture was heated to 50° and 4.6 ml of benzyl bromide was added. The mixture was cooled to room temperature, quenched by the addition of water, and concentrated. The concentrate was diluted with water and then extracted with diethyl ether. The combined extracts were washed with water, dried over anhydrous sodium sulfate and concentrated to an oil. Purification of the oil by high pressure liquid chromatography utilizing diethyl ether/hexane (1:99) yielded 10.5 g (72%) of 4-benzyloxy-1-nonadecene as a liquid.

ANALYSIS: Calculated for $C_{26}H_{44}O$: 83.80%C; 11.90%H; Found: 83.29%C; 11.88%H.

Step 3

To 66 ml of a 0.5M solution of 9-borabicyclo[3.3.1-]nonane in tetrahydrofuran, was added dropwise, under nitrogen, a solution of 11.1 g of 4-benzyloxy-1-nonadecene in 20 ml of dry tetrahydrofuran. The reaction mixture was stirred at room temperature for 2 hours, then quenched by the successive addition of 18 ml of ethanol, 6 ml of 6N sodium hydroxide solution, and 13 ml of 30% hydrogen peroxide. The mixture was maintained at 50° for 2 hours. Upon standing the mixture formed aqueous and organic phases. The aqueous phase was saturated with potassium carbonate, and the organic phase was separated, washed with 25 ml of a 10% aqueous solution of sodium sulfite and 25 ml of a saturated aqueous solution of sodium chloride, dried over anhydrous potassium carbonate, and concentrated. The concentrate was taken up in 20% diethyl ether/hexane, filtered and concentrated to give 11.5 g of an oil. Flash chromatography of the oil on silica gel using as an eluent hexane/diethyl ether (2:1 by volume) yielded 10.3 g of 4-benzyloxynonadecan-1-ol as an oil.

ANALYSIS: Calculated for $C_{26}H_{46}O_2$: 79.94%C; 11.87%H; Found 80.00%C; 12.04%H.

Step 4

A reaction mixture formed by the dropwise addition of 3.65 g of neat 2-chloro-2-oxo-1,3,2-dioxaphospholane to an anhydrous solution of 10.0 g of 4-benzyloxynonadecan-1-ol and 4.2 ml of triethylamine in 200 ml of toluene was stirred at room temperature overnight, filtered, and concentrated to give 11.9 g of an oil. The oil was dissolved in 150 ml of acetonitrile and added to a pressure reactor. Trimethylamine (9 g) was condensed into the reactor, under nitrogen, at about −15°. The reactor was then sealed and heated at 70°–80° for 24 hours. Cooling the reaction mixture in ice precipitated a solid. The solid was collected, washed with acetone, taken up in chloroform/benzene and concentrated to a residue. The residue was purified by flash chromatography on silica using as successive eluents chloroform/methanol (9:1 by volume) and chloroform/methanol/water (120:30:4 by volume) to give 7.4 g of 4-hydroxy-N,N,N-trimethyl-9-phenylmethoxy-3,5-dioxa-4-phosphatetracosan-1-aminium, 4-oxide, hydroxide, inner salt monohydrate, as a waxy solid.

ANALYSIS: Calculated for $C_{31}H_{58}NO_5P.H_2O$: 64.89%C; 10.54%H; 2.44%N; 5.39%P; Found: 65.29%C; 10.46%H; 2.45%N; 5.05%P.

EXAMPLE 5

4-Hydroxy-N-methyl-3,5-dioxa-9-phenylmethoxy-4-phosphatetracosan-1-pyrrolidinium, 4-oxide, hydroxide, inner salt dihydrate To an anhydrous solution of 10 g of 4-benzyloxynonadecan-1-ol (prepared as in Step 2 of Example 4) and 4.2 ml of triethylamine in 200 ml of toluene was added dropwise, under nitrogen, 3.65 g of 2-chloro-2-oxo-1,3,2-dioxaphospholane. The mixture was stirred at room temperature overnight, filtered, and concentrated. The residue was combined with 8.0 ml of N-methylpyrrolidine and 120 ml of anhydrous acetonitrile, and refluxed under nitrogen for 28 hours. Concentration of the mixture gave 17.4 g of an oil. Flash chromatography of the oil using as successive eluents chloroform/methanol (9:1 by volume) and chloroform/methanol/water (120:30:4 by volume) gave 9.4 g of 4-hydroxy-N-methyl-3,5-dioxa-9-phenylmethoxy-4-phosphatetracosan-1-pyrrolidinium, 4-oxide, hydroxide, inner salt dihydrate as a wax.

ANALYSIS: Calculated for $C_{33}H_{60}NO_5P.2H_2O$: 64.15%C; 10.44%H; 2.27%N; 5.16%P; Found: 63.92%C; 10.16%H; 2.61%N; 5.18%P;

EXAMPLE 6

4,9-Dihydroxy-N-methyl-3,5-dioxa-4-phosphatetracosan-1-pyrrolidinium, 4-oxide, hydroxide, inner salt 3.5 hydrate A solution of 4.3 g of 4-hydroxy-N-methyl-3,5-dioxa-9-phenylmethoxy-4-phosphatetracosan-1-pyrrolidinium, 4-oxide, hydroxide, inner salt dihydrate (prepared as in Example 5) in 125 ml of ethanol and 60 ml of acetic acid was hydrogenated in a Parr apparatus in the presence of 0.6 g of 5% palladium-on-carbon at 25 psi for 16 hours. Filtration, concentration and azeotroping with chloroform/toluene yielded a residue which was triturated with 200 ml of diethyl ether/hexane (1:1 by volume) to give 3.2 g of a solid. Flash chromatography of the solid using as successive eluents chloroform/methanol (9:1 by volume) and chloroform/methanol/water (120:30:4 by volume) gave 2.7 g of 4,9-dihydroxy-N-methyl-3,5-dioxa-4-phosphatetracosan-1-pyrrolidinium, 4-oxide, hydroxide, inner salt 3.5 hydrate as a solid.

ANALYSIS: Calculated for $C_{26}H_{54}NO_5P.3.5H_2O$: 56.29%C; 11.08%H; 2.52%N; 5.58%P; Found: 56.58%C; 10.49%H; 2.54%N; 5.65%P;

EXAMPLE 7

4,9-Dihydroxy-N,N,N-trimethyl-3,5-dioxa-4-phosphatetracosan-1-aminium, hydroxide, inner salt sesquihydrate A solution of 4.9 g of 4-hydroxy-N,N,N-trimethyl-9-phenylmethoxy-3,5-dioxa-4-phosphatetracosan-1-aminium, 4-oxide, hydroxide, inner salt monohydrate in 150 ml of ethanol was treated overnight, at room temperature in an atmospheric hydrogenator in the presence of 0.6 g of 5% palladium on carbon. A volume of 217 ml of hydrogen was consumed. The solution was filtered, diluted with 10 ml of water, and concentrated. Azeotroping of the concentrate with toluene yielded 3.8 g (90%) of 4-hydroxy-N,N,N-trimethyl-9-phenylmethoxy-3,5-dioxa-4-phosphatetracosan-1-aminium, 4-oxide, hydroxide, inner salt as a solid, mp. 239–242° (dec).

ANALYSIS: Calculated for $C_{24}H_{52}NO_5P.1.5H_2O$: 58.51%C; 11.25%H; 2.84%N; 6.27%P; 58.25%C; 11.03%H; 2.67%N; 6.24%P.

EXAMPLE 8

4-Hydroxy-N,N,N-trimethyl-9-phenylmethoxy.3,5-dioxa-4phosphapentacosan-1-aminium, 4-oxide, hydroxide, inner salt 1.25 hydrate

Step 1

To a refluxing mixture of 1.26 g of magnesium turnings, 15.5 ml of 1-chlorohexadecane, and 100 ml of anhydrous diethyl ether were added 0.5 ml of a 3.2 M solution of methylmagnesium bromide in diethyl ether and 0.05 ml of ethyl bromide. The reaction mixture was refluxed for a period of 6 hours. A solution of 3.0 g of 4-[(tetrahydro-2H-pyran-2-yl)oxy]butanal in 10 ml of diethyl ether was added, and the reaction mixture refluxed for an additional hour. The reaction mixture was poured into a mixture of ice and a saturated aqueous solution of ammonium chloride, and filtered. Upon standing the filtrate separated into organic and inorganic phases. The organic phase was dried over anhydrous sodium sulfate and concentrated to an oil. Flash chromatography of the oil utilizing 25% diethyl ether/petroleum ether yielded 4.8 g (70%) of 1-[(tetrahydro-2H-pyran-2-yl)oxy]eicosan-4-ol as a solid, mp 39–43°.

ANALYSIS: Calculated for $C_{25}H_{50}O_3$: 75.32%C; 12.64%H; Found: 75.47%C; 12.68%H.

To a suspension of hexane washed sodium hydride (from 0.34 g of a 50% oil dispersion) in 5 ml of tetrahydrofuran was added a solution of 2.4 g of 1-[(tetrahydro-2H-pyran-2-yl) oxy]eicosan-4-ol (prepared as in Step 1) in 10 ml of tetrahydrofuran. Following the evolution of hydrogen, 66 mg of tetrabutylammonium iodide and 0.83 ml of benzyl bromide were added, and the reaction mixture was refluxed, under nitrogen, for three days. The reaction mixture was then diluted with water. Upon standing the mixture formed aqueous and organic phases. The aqueous phase was extracted with diethyl ether. The extract was then combined with the organic phase and evaporated. The residue was dissolved in diethyl ether, washed with water, dried over anhydrous sodium sulfate and evaporated to give 3.0 g of an oil. The oil was purified by means of flash chromatography utilizing as the eluent 5–10% ethyl ether/petroleum ether, to yield 2.2 g of 4-benzyloxy-1-[(tetrahydro-2H-pyran-2-yl)oxy]eicosane as an oil.

The reaction was repeated on the same scale without tetrabutylammonium iodide using dimethylformamide as the solvent and heating the mixture, under nitrogen, at 50° for 24 hours. Workup in a similar manner gave 2.5 g of 4-benzyloxy-1-[(tetrahydro-2H-pyran-2-yl)oxy]eicosane as an oil. The combined products of both reactions were chromatographed by high pressure liquid chromatography utilizing 10% diethyl ether/dichloromethane as the eluent to yield 3.5 g (60%) of 4-benzyloxy-1-[(tetrahydro-2H-pyran-2-yl)oxy]eicosane.

ANALYSIS: Calculated for $C_{32}H_{56}O_3$: 78.63%C; 11.55%H; Found: 78.39%C; 11.54%H;

Step 3

A solution of 11.5 g of 4-benzyloxy-1-[(tetrahydro-2H-pyran-2-yl)oxy]eicosane (prepared as described in Step 2) in 200 ml of ethanol was treated with 5 drops of 5N hydrochloric acid and heated to 50° for 2 hours. The reaction mixture was then neutralized with sodium bicarbonate and concentrated. The concentrate was extracted with diethyl ether. The extract was washed with water and a saturated solution of sodium chloride, dried over anhydrous sodium sulfate and evaporated to give 9.7 g of an oil. The oil was purified by means of high pressure liquid chromatography utilizing as an eluent 25% diethyl ether/petroleum ether to give 2.9 g (90%) of 4-benzyloxyeicosan-1-ol as an oil.

ANALYSIS: Calculated for $C_{27}H_{48}O_2$: 80.14%C; 11.96%H; Found: 80.23%C; 12.22%H;

Step 4

To an anhydrous solution of 11.43 g of 4-benzyloxyeicosan-1-ol and 6.4 ml of triethylamine in 300 ml of toluene was added, dropwise, under nitrogen, 4.02 g of 2-chloro-oxo-1,3,2-dioxaphospholane. The reaction mixture was stirred at ambient temperature overnight, filtered, and concentrated to yield 15.65 g of an oil. The oil was dissolved in 150 ml of acetonitrile and added to a pressure reactor. Trimethylamine (26 g) was condensed into the reactor, under nitrogen, at a temperature of −40°. The reactor was then sealed and heated to 80° for 24 hours. Cooling the reaction mixture in an ice bath precipitated a solid. The solid was taken up in chloroform and concentrated. Flash chromatography of the residue using as successive eluents chloroform/methanol (9:1 by volume) followed by chloroform/methanol/water, (120:30:4 by volume), yielded 4.67 g (28%) of 4-hydroxy-N,N,N-trimethyl-9-phenylmethoxy-3,5-dioxa-4-phosphapentacosan-1-aminium-4-oxide, hydroxide inner salt 1.25 hydrate as a waxy solid.

ANALYSIS: Calculated for $C_{32}H_{60}NO_5P\cdot1.25H_2O$: 64.88%C; 10.64%H; 2.37%N; 5.23%P; Found: 64.52%C; 10.48%H; 2.39%H; 5.11%P.

EXAMPLE 9

4,9-Dihydroxy-N,N,N-trimethyl-3,5-dioxa-4-phosphopentacosan-1-aminium, 4-oxide, hydroxide, inner salt monohydrate A mixture of 3.3 g of 4-hydroxy-N,N,N-trimethyl-9-phenylmethoxy-3,5-dioxa-4-phosphapentacosan-1-aminium, 4-oxide, hydroxide, inner salt 1.25 hydrate, 125 ml of ethanol and 0.4 g of 5% palladium on carbon was hydrogenated at 50 psi for 5 hours. The reaction mixture was filtered, treated with 2 ml of water and concentrated. Azeotroping with toluene yielded 2.55 g (92%) of 4,9-dihydroxy-N,N,N-trimethyl-3,5-dioxa-4-phosphopentacosan-1-aminium, 4-oxide, hydroxide, inner salt monohydrate, mp 240°–242°.

ANALYSIS: Calculated for $C_{25}H_{54}NO_5P\cdot H_2O$: 60.33%C; 10.94%H; 2.815N; 6.23%P; Found: 60.18%C; 11.17%H; 2.70%N; 6.14%P;

EXAMPLE 10

4-Hydroxy-N,N,N-trimethyl-9-phenylmethoxy.3,5-dioxa-4phosphahexacosan-1-aminium, 4-oxide, hydroxide, inner salt monohydrate Step 1

To a 1M solution of allylmagnesium bromide in diethyl ether (15 ml) was added dropwise, a solution of 4.0 g of octadecanal in 20 ml of tetrahydrofuran. The reaction mixture was allowed to stand at room temperature for 16 hours. The reaction mixture was then poured into a mixture of ice and water, acidified to a pH of 2 by the addition of a 5% aqueous solution of hydrochloric acid and concentrated. The concentrate was extracted with diethyl ether. The extract was washed with water, dilute aqueous solutions of sodium bicarbonate and sodium chloride, dried, and evaporated to yield an oil. Flash chromatography of the oil utilizing 10% diethyl ether/petroleum ether gave a wax. High pressure liquid chromatography of the wax utilizing 5% diethyl ether/petroleum ether as the eluent yielded 2.8 g (61%) of 1-heneicosan-4-ol, mp 48.0°–50.5°.

ANALYSIS: Calculated for $C_{21}H_{42}O$: 81.21%C; 13.63%H; Found 81.28%C; 13.88%H.

Step 2

To hexane washed sodium hydride (from 2.56 g of a 50% oil dispersion) was added dropwise, under nitrogen, a solution of 11.0 g of 1-heneicosen-4-ol in 60 ml of dimethylformamide. The solution was heated to 50° and 4.4 ml of benzyl bromide was added. The reaction mixture was then cooled to room temperature, combined with 300 ml of a water-ice mixture, and extracted with hexane. The extract was dried over anhydrous magnesium sulfate and concentrated, in vacuo, to a liquid. High pressure liquid chromatography of the liquid utilizing as an eluent 0.5% diethyl ether/hexane yielded 8.2 g (57%) of 4-benzyloxy-1-heneicosene.

ANALYSIS: Calculated for $C_{28}H_{48}O$: 83.93%C; 12.08%H; Found: 83.55%C; 11.99%H.

Step 3

To a 33 ml solution of a 0.5M solution of 9-borabicyclo[3:3:1]nonane in tetrahydrofuran was added dropwise, under nitrogen, a solution of 6.0 g of 4-benzyloxy-1-heneicosene in 30 ml of dry tetrahydrofuran. After stirring at room temperature for 3 hours, the reaction was quenched by successive addition of 9 ml of ethanol, 3 ml of 6N sodium hydroxide and 6.5 ml 30% hydrogen peroxide. The reaction mixture was heated at 50° for 90 minutes and then allowed to stand at ambient temperature overnight. Upon standing, the reaction mixture separated into aqueous and organic phases. The aqueous phase was saturated with potassium carbonate, and the organic phase was separated, washed with 15 ml of 10% solution of sodium sulfite and 20 ml of saturated solution of sodium chloride, dried over potassium carbonate, and concentrated. The residue was taken up in a mixture of 20% diethyl ether/hexane, filtered and concentrated to an oil. Flash chromatography of the oil on silica gel using hexane/diethyl ether (2:1 by volume) as the eluent gave 4.88 g (78%) of 4-benzyloxyheneicosan-1-ol.

ANALYSIS: Calculated for $C_{28}H_{50}O_2$: 80 32%C; 12.09%H; Found: 79.82%C; 12.21%H.

Step 4

To an anhydrous solution of 5 g of benzyloxyheneicosan-1-ol in 150 ml of dry toluene was added dropwise, under nitrogen, 1.71 g of neat 2-chloro-2-oxo-1,3,2-dioxaphospholane. The reaction mixture was stirred at ambient temperature overnight, filtered and concentrated. The residue was dissolved in 100 ml of acetonitrile and added to a pressure reactor. Trimethylamine (9.22 g) was condensed into the pressure reactor, under nitrogen, at a temperature of −40° C. The reactor was then sealed and heated to a temperature of 70°-80° C. for 48 hours. Cooling the reaction mixture with ice precipitated a solid. The solid was taken up in chloroform and concentrated. Flash chromatography of the residue using as successive eluents a mixture of chloroform/methanol (9:1 by volume), and chloroform/methanol/water (120:30:4 by volume) gave 1.18 g (19%) of 4-hydroxy-N,N,N-trimethyl-9-phenylmethoxy-3,5-dioxa-4-phosphahexacosan-1-aminium, 4-oxide, hydroxide, inner salt monohydrate as a waxy solid.

ANALYSIS: Calculated for $C_{33}H_{62}NO_5P.H_2O$: 65.85%C; 10.71%H; 2.33%N; 5.15%P; Found; 65.24%C; 10.66%H; 2.24%N; 5.19%P.

EXAMPLE 11

4-Hydroxy-N,N,N-trimethyl-9-phenylmethoxy-3,5-dioxa-18-phenyl-4-phosphaoctadecan-1-aminium, 4-oxide, hydroxide, inner salt trihydrate

Step 1

A solution of 20 g of 11-phenyl-1-undecene in 600 ml of dry toluene was cooled to −45° C. Ozone was bubbled through the cooled solution at a rate of 1.6 mmol/min for 49 minutes. The solution was warmed to room temperature, under nitrogen, and then transferred to a hydrogenation flask containing 1 g of 10% palladium-on-carbon and 200 g of 4A molecular sieves This mixture was hydrogenated for 3 hr at 50 psi, filtered and concentrated to give 18.26 g of 10-phenyldecanal.

Step 2

To a cooled solution of 1M allyl magnesium bromide in diethyl ether was added dropwise, under nitrogen, a solution of 18.2 g of 10-phenyldecanal (prepared as in Step 1) in 200 ml of dry tetrahydrofuran. The reaction mixture was stirred at about 5° for 15 minutes, at room temperature for 1 hour, and then at reflux for 15 minutes. The reaction mixture was cooled to room temperature and poured into a mixture of 400 g of ice and 40 ml of 9M sulfuric acid. Upon standing the mixture separated into aqueous and organic layers. The organic layer was stirred for 15 min with solid sodium bicarbonate and then concentrated. The aqueous layer was extracted with diethyl ether (2×200 ml) and the extracts were combined with the concentrated organic layer. The combined organics were washed with water (300 ml) and a half-saturated aqueous solution of sodium chloride (300 ml), dried over anhydrous magnesium sulfate, filtered and concentrated to an oil. High pressure liquid chromatography of the oil using 10% diethyl ether/hexane as the eluent gave 6.98 g (30%) of 13-phenyl-1-tridecen-4-ol as an oil.

ANALYSIS: Calculated for $C_{19}H_{30}O$: 83.15%C; 11.02%H; Found: 82.79%C; 11.23%H.

Step 3

To hexane-washed sodium hydride (from 0.92 g of a 50% oil dispersion) was added dropwise, under nitrogen, a solution of 4.06 g of 13-phenyl-1-tridecen-4-ol in 50 ml of tetrahydrofuran. The solution was heated to 50° and 2.79 g of benzyl bromide was added, dropwise. The reaction mixture was refluxed for 4 hours, quenched by the addition of 10 ml of water, and concentrated. The residue was extracted with hexane/diethyl ether (2:1 by volume) (3×100 ml), washed with 300 ml of water and 300 ml of a saturated aqueous solution of sodium chloride, and dried over anhydrous magnesium sulfate. Concentration gave 5.51 g of an oil which was chromatographed by high pressure liquid chromatography to yield 3.09 g (58%) of 4-benzyloxy-13-phenyl-1-tridecene as an oil.

ANALYSIS: Calculated for $C_{26}H_{36}O$: 85.66%C; 9.95%H; Found: 85.44%C; 9.95%H.

Step 4

To a 0.5M solution of 9-borabicyclo[3.3.1]nonane in tetrahydrofuran (253 ml) was added dropwise, under nitrogen, a solution of 41.8 g of 4-benzyloxy-13-phenyl-1-tridecene in 100 ml of dry tetrahydrofuran. The mixture was stirred at room temperature for 3 hours, quenched by the sequential addition of 72 ml of ethanol, 24 ml of 6 N solution of sodium hydroxide, and 48 ml of a 30% solution of hydrogen peroxide. The mixture was heated at 50° for 2.5 hours. Upon standing at room temperature overnight, the mixture separated into aqueous and organic layers. The organic layer was washed with 100 ml of a 10% aqueous solution of sodium sulfite and 100 ml of a saturated aqueous solution of sodium chloride, dried over anhydrous potassium carbonate and concentrated. The concentrate was taken up in 20% diethyl ether/hexane, filtered and concentrated to an oil. The oil was purified by high pressure liquid chromatography using as an eluent hexane/diethyl ether (2:1 by volume) to give 32.7 g (75%) 4-benzyloxy-13-phenyl-tridecan-1-ol as an oil.

ANALYSIS: Calculated for $C_{26}H_{38}O_2$: 81.62%C; 10.01%H; Found: 81.45%C; 9.99%H.

Step 5

To a stirred solution of 12.6 g of 2-bromoethyl phosphorodichloridate in 200 ml of diethyl ether cooled to 0° C., was added dropwise, in the following order, 21 ml of pyridine, and a solution of 10 g of 4-benzyloxy-13-phenyl-tridecan-1-ol in 200 ml of diethyl ether. The mixture was stirred at 0° for 30 min and warmed to room temperature. Water (100 ml) was then added and the mixture stirred at room temperature for 1 hour. The mixture was acidified to a pH of 2 by the addition of 6 N hydrochloric acid. Upon standing the mixture formed aqueous and organic layers. The organic layer was washed with 250 ml of a saturated solution of sodium chloride, dried over anhydrous magnesium sulfate, and concentrated. To a solution of 14 g of concentrate in 130 ml of chloroform was added dropwise, in the following order, 210 ml of acetonitrile, and 409 ml of a 33% aqueous solution of trimethylamine. The solution was heated at 60° for 20 hours, and concentrated. The concentrate was refluxed with 1000 ml of methanol and 10 grams of silver carbonate for 2 hours, filtered, and concentrated. Flash chromatography of the concentrate using as successive eluents chloroform:methanol (9:1 by volume) and chloroform:methanol:water (120:30:4 by volume) gave 6.7 g (48%) of 4-hydroxy-N,N,N-trimethyl-9-phenylmethoxy-3,5-dioxa-18-phenyl-4-phosphaoctadecan-1-aminium, 4-oxide, hydroxide, inner salt trihydrate as a gum.

ANALYSIS:
Calculated for $C_{31}H_{50}NOP.3H_2O$: 61.87%C; 9.38%H; 2.33%N; 5.15%P; Found: 61.84%C; 9.15%H; 2.295N; 5.33%P.

EXAMPLE 12

4,9-Dihydroxy-N,N,N-trimethyl-3,5-dioxa-18-phenyl-4-phosphaoctadecan-1-aminium, 4-oxide, hydroxide, inner salt 2.5 hydrate A mixture of 5.8 g of 4-hydroxy-N,N,N-trimethyl-3,5-dioxa-18-phenyl-4-phosphaoctadecene-1-aminium, 4-oxide, hydroxide, inner salt trihydrate, 218 ml of ethanol, 35 ml of acetic acid and 0.8 g of 5% palladium-on-carbon was hydrogenated in a Parr apparatus for 24 hours at 56 psi. The mixture was filtered, concentrated, and azeotroped with toluene to give an oil. The oil was flash chromatographed using as successive eluents chloroform/methanol (9:1 by volume) and chloroform/methanol/water (120:30:4 by volume) to give 3.38 g (70%) of 4,9-dihydroxy-N,N,N-trimethyl-3,5-dioxa-18-phenyl-4-phosphaoctadecan-1-aminium, 4-oxide, hydroxide, inner salt 2.5 hydrate as a waxy solid, mp 220°-223°.

ANALYSIS: Calculated for $C_{24}H_{44}NO_5P.2.5H_2O$: 57.35%C; 7.83%H; 2.78%N; 6.16%P; Found: 56.9%C; 9.51%H; 2.99%N; 6.16%P.

EXAMPLE 13

4-Hydroxy-N,N,N-trimethyl-9-phenylmethoxy-3,5-dioxa-18-phenoxy-4-phosphaoctadecan-1-aminium, 4-oxide, hydroxide, inner salt monohydrate Step 1

Ozone was bubbled through a solution of 20 g of 11-phenoxy-1-undecene in 600 ml of anhydrous toluene cooled to −45° at a rate of 1.6 mmol/min for 49 min. The solution was warmed to room temperature and then transferred to a hydrogenation flask containing 1 g of 10% palladium on carbon and 200 g of 4A molecular sieves. The mixture was hydrogenated at 50 psi for 2 hours, filtered and concentrated to give 20.1 g of 10-phenoxydecanal.

Step 2

To 85 ml of a 1 M solution of allyl magnesium bromide in diethyl ether cooled in ice bath was added dropwise, under nitrogen, a solution of 20 g of 10-phenoxydecanal in 200 ml of dry tetrahydrofuran. The mixture was poured into 400 ml of ice and 30 ml of 9M sulfuric acid was added. Upon standing the mixture formed aqueous and organic layers. The organic layer was stirred for 15 min with solid sodium bicarbonate and concentrated. The aqueous layer was extracted with diethyl ether (2×200 ml) and the extracts were combined with the concentrated organic layer. The combined organics were washed with 300 ml of water and 300 ml of a half-saturated aqueous solution of sodium chloride, filtered, and concentrated. The residue was flash chromatographed utilizing as successive eluents 5% diethyl ether/hexane, 10% diethyl ether/hexane, and 25% diethyl ether/hexane to give 18.51 g (42%) of 13-phenoxy-1-tridecen-4-ol as a solid, m.p. 50°-52°.

ANALYSIS: Calculated for $C_{19}H_{30}O_2$: 78.57%C; 10.41%H; Found: 78.61%C; 10.38%H.

Step 2

To hexane-washed sodium hydride (from 1.39 g of a 50% oil dispersion) was added dropwise, under nitrogen, a solution of 6.46 g of 13-phenoxy-1-tridecen-4-ol in 25 ml of dry tetrahydrofuran. The solution was warmed to 50° C. and a solution of 2.91 ml of benzyl bromide in 25 ml of dimethylformamide was added. The mixture was refluxed for 4 hours, cooled to room temperature, and quenched with 10 ml of water, and concentrated. The concentrate was extracted with hexane/diethyl ether (2:1 by volume) (3×100 ml). The combined extracts were washed with water (200 ml) and a saturated aqueous solution of sodium chloride (200 ml), dried over anhydrous magnesium sulfate and concentrated to an oil. The oil was chromatographed by high pressure liquid chromatography using diethyl ether:hexane (1:49 by volume) to give 6.34 g (75%) of 4-benzyloxy-13-phenoxy-1-tridecene.

ANALYSIS: Calculated for $C_{26}H_{26}O_2$: 82.05%C; 9.59%H; Found: 82.08%C; 9.53%H.

Step 3

To 388 ml of a 0.5 M solution of 9-borabicyclo[3.3.1]nonane in tetrahydrofuran was added dropwise, under nitrogen, a solution of 66.3 g of 4-benzyloxy-13-phenoxy-1-tridecene in 100 ml of tetrahydrofuran. The solution was stirred for 3 hours, then quenched by the sequential addition of 98 ml of ethanol, 34 ml of a 6 N solution of sodium hydroxide and 70 ml of 30% hydrogen peroxide. The mixture was heated at 50° for 3 hours and then allowed to stand at room temperature overnight. Upon standing the mixture formed aqueous and organic layers. The organic layer was washed with 100 ml each of a 10% aqueous solution of sodium sulfite and a saturated aqueous solution of sodium chloride, dried over anhydrous potassium carbonate and concentrated. The residue was taken up in a mixture of diethyl ether:hexane (1:4), filtered, and concentrated to give 68.35 g of an oil. High pressure liquid chromatography of 24 g of the oil using as an eluent hexane/diethyl ether (2:1 by volume) gave 19.02 g (77%) of 4-benzyloxy-13-phenoxy-tridecan-1-ol as an oil.

Step 4

To a solution of 6.5 g of 4-benzyloxy-13-phenoxytridecan-1-ol in 60 ml of carbon tetrachloride was added dropwise, in the following order, 4.7 g of 2-bromoethyl phosphodichloridate and 2.7 ml of triethylamine. The mixture was stirred at room temperature for 2.5 hours, filtered, and concentrated. The residue was taken up in 60 ml of tetrahydfuran, and 60 ml of a 0.5 M sodium acetate was added. The mixture was stirred at room temperature for 60 hours, quenched by the addition of 20 ml of a 5% aqueous solution of hydrochloric acid and 30 ml of a saturated aqueous solution of sodium chloride, and extracted with ethyl acetate (3×100 ml). The combined extracts were dried over anhydrous magnesium sulfate and concentrated. Flash chromatography of the concentrate using 5% methanol/chloroform as the eluent gave 3.4 g (30%) of 2-bromoethyl (4-benzyloxy-13-phenoxytridecan-1-yl)phosphate.

A solution of 2-bromoethyl (4-benzyloxy-13-phenoxytridecan-1-yl)phosphate (3.21 g) in 23.2 ml of chloroform, 37.5 ml of isopropanol, 37.5 ml of acetonitrile and 72.7 ml of a 33% aqueous solution of trimethylamine was stirred at 50° for 20 hours. The mixture was concentrated, and the concentrate purified by flash chromatography using as successive eluents chloroform/methanol (9:1 by volume) and chloroform/methanol/5% aqueous ammonium hydroxide (13:7:1 by volume) to give 3.14 g of the hydrobromide. The hydrobromide was taken up in 50 ml of methanol and 1.5 g of silver carbonate was added. The mixture was refluxed for 2 hours, filtered and concentrated to a gum. Flash chromatography of the gum using as successive eluents chloroform/methanol (9:1 by volume) and chloroform/methanol/water (65:25:4 by volume) gave 2.08 g of 4-hydroxy-N,N,N-trimethyl-9-phenylmethoxy-3,5-dioxa-18-phenoxy-4-phosphaoctadecan-1-aminium, 4-oxide, hydroxide, inner salt monohydrate as a solid, m.p. 173°–175°:

ANALYSIS: Calculated for $C_{31}H_{50}NO_6P \cdot H_2O$: 64.00%C; 8.70%H; 2.41%N; 5.32%P; Found: 63.70%C; 8.93%H; 2.34%N; 5.33%P.

EXAMPLE 14

4,9-Dihydroxy-N,N,N-trimethyl-3,5-dioxa-18-phenoxy-4-phosphaoctadecan-1-aminium, 4-oxide, hydroxide, inner salt dihydrate A mixture of 12 g of 4-hydroxy-N,N,N-trimethyl-9-phenylmethoxy-3,5-dioxa-18-phenyoxy-4-phosphaoctadecan-1-aminium, 4-oxide, hydroxide, inner salt monohydrate, 150 ml of ethanol, 50 ml of acetic acid and 1.5 g of 5% palladium on carbon was hydrogenated for 20 hours at 56 psi, filtered and concentrated. Flash chromatography of the residue using as successive eluents chloroform/methanol (9:1 by volume) and chloroform/methanol/water (120:30:4 by volume) gave 7.9 g (74%) of 4,9-dihydroxy-N,N,N-trimethyl-3,5-dioxa-18-phenoxy-4-phosphaoctadecan-1-aminium, 4-oxide, hydroxide, inner salt dihydrate as a solid.

ANALYSIS: Calculated for $C_{24}H_{44}NO_6P \cdot 2H_2O$: 56.56%C; 9.49%H; 2.74%N; 6.07%P; Found: 56.48%C; 9.14%H; 2.91%N; 6.14%P.

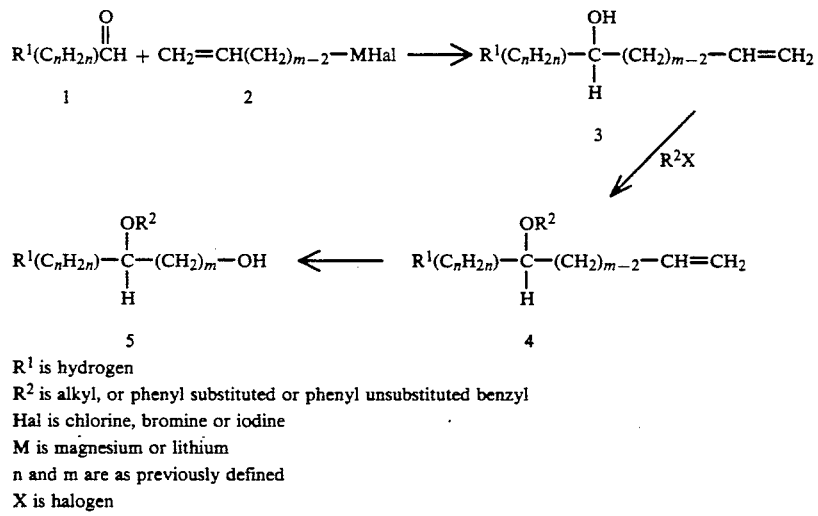

REACTION SCHEME A $R^1$ is hydrogen
$R^2$ is alkyl, or phenyl substituted or phenyl unsubstituted benzyl
Hal is chlorine, bromine or iodine
M is magnesium or lithium
n and m are as previously defined
X is halogen

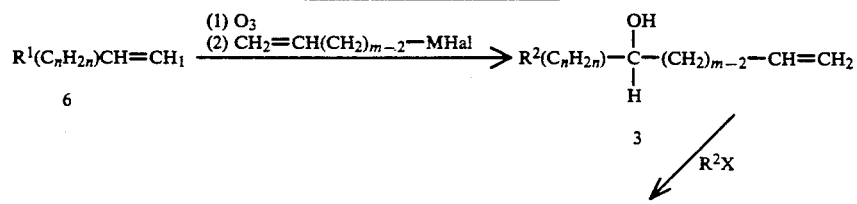

REACTION SCHEME B

REACTION SCHEME B

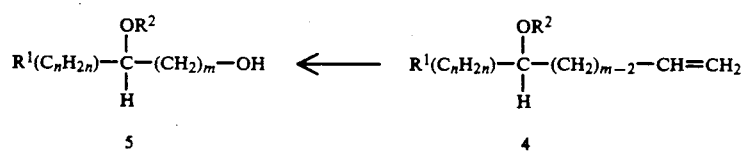

R[1] is phenyl or phenoxy
R[2] is alkyl, phenyl substituted or phenyl unsubstituted benzyl
Hal is chlorine, bromine or iodine
M is magnesium or lithium
m and n are as previously defined
X is halogen

REACTION SCHEME C

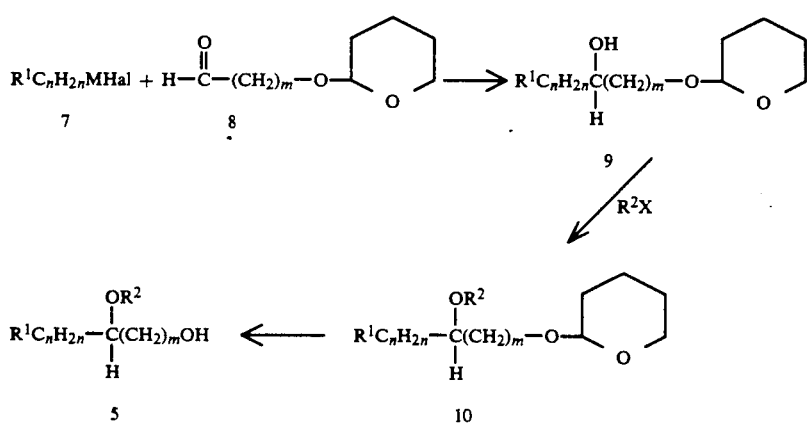

R[1] is hydrogen
R[2] is alkyl, or phenyl substituted or phenyl unsubstituted benzyl
Hal is chlorine, bromine or iodine
M is magnesium or lithium
m and n are as previously defined
X is halogen

REACTION SCHEME D

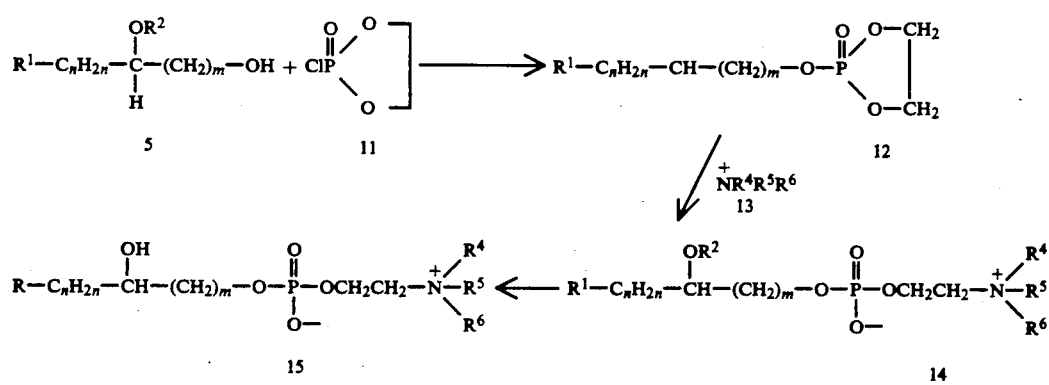

R[1] is hydrogen, phenyl, or phenoxy
R[2] is alkyl or phenyl substituted or phenyl unsubstituted benzyl
n, m, R[4], R[5] and R[6] are as previously defined

REACTION SCHEME E

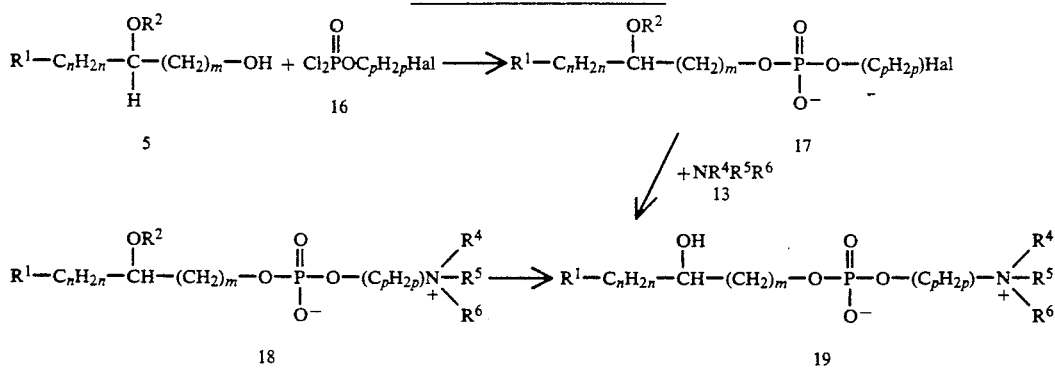

R¹ is hydrogen, phenyl, or phenoxy
R² is alkyl or phenyl substituted or phenyl unsubstituted benzyl
Hal is chlorine, bromine or iodine
n, m, p, R⁴, R⁵ and R⁶ are as previously defined what is claimed is:

1. A method of treating a patient having a phospholipase $A_2$ mediated condition comprising administering to said patient an effective amount of phospholipase $A_2$ inhibiting compound of the formula

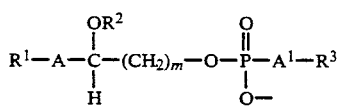

wherein R¹ is selected from the group consisting of hydrogen,

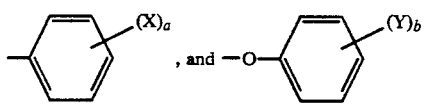

wherein a is an integer having a value of 0 to 2, inclusive, X is selected from the group consisting of alkyl radicals having 1 to 6 carbon atoms, inclusive, alkoxy radicals having 1 to 6 carbon atoms, inclusive, halogen, hydroxy and trifluoromethyl radicals, b is an integer having a value from 0 to 2, inclusive, and Y is selected from the group consisting of alkyl radicals having 1 to 6 carbon atoms, inclusive, alkoxy radicals having 1 to 6 carbon atoms, inclusive, halogen, hydroxy and trifluoromethyl radicals; R² is selected from the group consisting of hydrogen, alkyl radicals having up to 6 carbon atoms inclusive, and

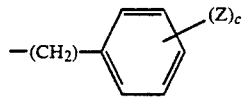

wherein c is an integer having a value of 0 to 1 and Z is an alkoxy radical having 1 to 6 carbon atoms; R³ is

wherein R⁴ is an alkyl radical having up to 6 carbon atoms, inclusive, R⁵ and R⁶ are independently alkyl radicals having up to 6 carbon atoms, inclusive, or, taken together with the nitrogen atom to which they are attached form a group of the formula

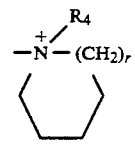

wherein r is 0 or 1; A is a bivalent radical of the formula $-C_nH_{2n}-$ wherein n is an integer having a value from 1 to 20, inclusive, and m is an integer is an integer having a value of 3 or 4; and A¹ is a bivalent radical of the formula $-C_pH_{2p}-$ wherein p is an integer having a value from 2 to 10, inclusive, with the proviso that the sum of n and p does not exceed 25; the geometrical isomers, or optical antipodes thereof.

2. A phospholipase $A_2$ inhibiting composition comprising an inert phospholipase $A_2$ inhibiting adjuvant and, as the active ingredient, an amount effective in phospholipase $A_2$ inhibition of a compound as defined in claim 1.

3. A method of alleviating pain in a mammal which comprises administering to a mammal a pain alleviating effective amount of a compound as defined in claim 1.

* * * * *